United States Patent [19]

Weibel et al.

[11] Patent Number: 5,385,640
[45] Date of Patent: Jan. 31, 1995

[54] PROCESS FOR MAKING MICRODENOMINATED CELLULOSE

[75] Inventors: Michael K. Weibel, West Redding; Richard S. Paul, Redding, both of Conn.

[73] Assignee: Microcell, Inc., West Redding, Conn.

[21] Appl. No.: 89,683

[22] Filed: Jul. 9, 1993

[51] Int. Cl.⁶ .................................................. D21B 1/10
[52] U.S. Cl. ........................................ 162/23; 241/21; 241/28
[58] Field of Search ............... 162/23, 100; 241/21, 241/28

[56] References Cited

U.S. PATENT DOCUMENTS

| | | | |
|---|---|---|---|
| 238,044 | 2/1881 | Luckenbach et al. | |
| 1,631,834 | 6/1927 | Schorger | 162/187 |
| 2,054,301 | 9/1936 | Richter | 162/187 |
| 2,885,154 | 5/1959 | Du Bois Eastman et al. | 241/5 |
| 3,023,104 | 2/1962 | Battista | 99/1 |
| 3,186,648 | 6/1965 | Mandle et al. | 241/34 |
| 3,467,317 | 9/1969 | Stephanoff | 241/5 |
| 3,643,875 | 2/1972 | Dille et al. | 241/5 |
| 3,701,484 | 10/1972 | Donovan | 241/39 |
| 3,808,090 | 4/1974 | Logan et al. | 162/23 |
| 4,087,317 | 5/1978 | Roberts | 162/187 |
| 4,143,163 | 3/1979 | Hutchison et al. | 426/96 |
| 4,173,248 | 11/1979 | Roberts | 162/141 |
| 4,216,242 | 8/1980 | Braverman | 426/573 |
| 4,261,521 | 4/1981 | Ashbrook | 241/5 |
| 4,269,859 | 5/1981 | Morse | 424/362 |
| 4,336,370 | 6/1982 | Yasnovsky et al. | 536/58 |
| 4,341,807 | 7/1982 | Turbak et al. | 426/570 |
| 4,374,702 | 2/1983 | Turbak et al. | 162/100 |
| 4,378,381 | 3/1983 | Turbak et al. | 426/570 |
| 4,385,172 | 5/1983 | Yasnovsky et al. | 536/70 |
| 4,452,722 | 6/1984 | Turbak et al. | 252/311 |
| 4,464,287 | 8/1984 | Turbak et al. | 252/49.5 |
| 4,481,076 | 11/1984 | Herrick | 162/187 |
| 4,481,077 | 11/1984 | Herrick | 162/9 |
| 4,483,743 | 11/1984 | Turbak et al. | 162/158 |
| 4,487,634 | 12/1984 | Turbak et al. | 106/203 |
| 4,500,546 | 2/1985 | Turbak et al. | 424/362 |
| 4,533,254 | 8/1985 | Cook et al. | 336/176 |
| 4,543,410 | 9/1985 | Cruz, Jr. | 536/84 |
| 4,645,606 | 2/1987 | Ashbrook et al. | 210/695 |
| 4,659,388 | 4/1987 | Innami et al. | 106/163.1 |
| 4,680,189 | 7/1987 | Schumacher et al. | 426/285 |
| 4,692,211 | 9/1987 | Roberts | 162/187 |
| 4,710,390 | 12/1987 | Schumacher et al. | 426/285 |
| 4,761,203 | 8/1988 | Vinson | 162/9 |
| 4,764,283 | 8/1988 | Ashbrook et al. | 210/695 |
| 4,780,321 | 10/1988 | Levy et al. | 424/499 |
| 4,863,565 | 9/1989 | Johnson et al. | 162/150 |
| 4,908,154 | 3/1990 | Cook et al. | 252/314 |
| 5,026,569 | 6/1991 | Forand | 426/599 |
| 5,073,397 | 12/1991 | Tarr et al. | 426/599 |
| 5,269,470 | 12/1993 | Ishikawa et al. | 241/21 |

FOREIGN PATENT DOCUMENTS

| | | |
|---|---|---|
| 949464 | 2/1964 | United Kingdom . |
| 1300820 | 12/1972 | United Kingdom . |
| WO9119421 | 12/1991 | WIPO . |
| WO9119423 | 12/1991 | WIPO . |

Primary Examiner—W. Gary Jones
Assistant Examiner—Dean T. Nguyen
Attorney, Agent, or Firm—Dann, Dorfman, Herrell and Skillman

[57] ABSTRACT

A process for the production of mechanically disassembled cellulose and the resultant product, referred to as microdenominated cellulose (MDC). The product is characterized by a settled volume of greater than 50%, as determined on the basis of a 1% by weight suspension in water after twenty-four hours, and a water retention value of over 350%. MDC is useful as an ingredient in foods, pharmaceutical and cosmetic products.

7 Claims, 6 Drawing Sheets

PROCESS FOR MAKING MICRODENOMINATED CELLULOSE

This invention relates to microdenominated cellulose and to a process for its preparation.

BACKGROUND OF THE INVENTION

Since cellulose is the major structural constituent of most plant matter, it is natural that those interested in processing or refining such materials refer to them as cellulosics. However this general term connotes a multiplicity of meanings whereby each is qualified by descriptors frequently specific to the interest at hand. The commercial applications of processed plant matter to produce a refined cellulosic material are numerous and involve use in many nonanalogous arts. For example, refined celluloses are extensively used in paper and textile applications. Refined cellulose is also used in adhesives, food ingredients, industrial coatings and various other diverse applications. For each end use, the raw material, processing and final product(s) comprise a technological field essentially unique to itself.

In general, a wide variety of chemical, thermal and mechanical transformations are known in the art to refine, manipulate and modify cellulose for numerous purposes. The following hierarchical characterization has been devised to describe previously known technology relating to structural manipulation of refined cellulosic substances. This characterization serves the additional purpose of providing bases for distinction between the process of the present invention and the prior art.

The molecular level or primary structure of cellulose is the beta 1-4 glucan chain. All celluloses share this level of structure and it is the distinguishing difference between cellulose and other complex polysaccharides. The natural chain length is not known due to unavoidable modification and degradation which occurs during the disassembly to this level, but probably extends into the polymerization regimes of many thousands of glucan units. Transformations at this level of structure involve forming and breaking chemical bonds.

Secondary structure is considered to be submicroscopic strands formed from parallel, aligned assemblages of glucan chains. This level of organization is designated the microfibril. Microfibrils are spontaneously formed from a plurality of nascent glucan chains believed to be synthesized simultaneously by a complex, motile, biosynthetic organelle involved in the assembly of the primary plant cell wall. The microfibril is of sufficient size to be discernable with the electron microscope and depending on the plant species ranges in its major cross-sectional dimension from approximately 50 to 100 Angstroms. As with the beta-glucan chain, of which it is composed, the length is indeterminant. Noncovalent interactions, such as by hydrogen bonding, stabilize secondary structure. Because the interchain attraction is high, structural transformation is probably rare unless preceded by chemical modification of primary structure.

Tertiary structure is related to arrays and associations of microfibrils into sheets and larger stranded structures designated fibrils. The distinguishing features at this level of structure are sufficiently small that resolution is usually possible only via the electron microscope. However, some individual fibril assemblies are of sufficient gross cross-sectional dimension (0.1 to 0.5 microns or 10,000 to 50,000 Angstroms) to be discernible with the light microscope. Structural deformation at this level is largely mechanical and either organized (disassembly/denomination) or random (indiscriminate fracture/cleavage).

Lastly, quaternary structure deals with the construct of tertiary elements which form the primary and secondary cell wall. This level of structure defines the physical dimensions of the individual cell and any gross structural specialization required for physiological function of the differentiated cell. Examples are libriform, tracheid and parenchymal cell structure. Structural manipulation results from indiscriminent comminution and is the most commonly employed mechanical transformation practiced.

Conventional pulping of cellulosic materials is primarily concerned with chemi-thermomechanical processing of schlerenchymous or structural plant tissue to achieve individually dispersed cells. The result is a quaternary structure largely consisting of cellulose derived from the primary and secondary cell walls. Depending on the plant source and extent of processing some heteropolysaccharides such as hemicellulose (xylans, galactomannans, pectins, etc.) may also be present. The important distinction of pulping from other processing of celluloses is that an anatomical destruction of intact plant tissue occurs. This results in dispersed cellforms which represent a minimal degree of quaternary and more basic structural levels of manipulation. Some forms of cellulose, such as cotton, are produced naturally in a dispersed state and do not require pulping as a prerequisite.

Important to the following discussion is the distinction between disassembly and indiscriminate fragmentation processes. In fragmentation the localized energy excursion (by whatever means) is sufficiently high and accumulates sufficiently rapidly that an organized dissipation of internal energy by the acquiring matrix is not effected. Here an intense perturbation is applied and results in an indiscriminate fracture or other major disorganization at translocations within a defined microdomain. In the case of disassembly, on the other hand, the acquired energy excursion is dissipated in a more organized manner usually following a path of lowest activation energy. For cellulose this appears to involve segmentation along parallel fibril oriented assemblies and possibly laminar sheet separation of fibril arrays.

Mechanically beaten celluloses have long been employed in the paper and packaging industry. Chemi-thermomechanically refined wood pulps are typically dispersed in hydrobeaters and then subjected to wet refining in high speed disc mills. This level of structural manipulation as presently practiced is exclusively at the quaternary level. The objective of such processing is to disperse aggregated fiber bundles and increase available surface area for contact during drying to increase dry strength. Substantial size reduction and concomitant impairment of dewatering are undesirable and circumscribe the extent of processing. The measurement of the ease of water drainage from a beaten pulp is termed Canadian Standard Freeness and reflects the ease or rate of interstitial water removal from the paper stock.

Finely ground or fragmented celluloses are well known. These products are produced by mechanical comminution or grinding of dried, refined cellulose. They are employed largely as inert, non-mineral fillers in processed foods and plastics. The manipulation is exclusively at the quaternary level of structure. It is achieved by application of a variety of size reduction technologies, such as ball and bar mills, high speed cutters, disc mills or other techniques described in part in U.S. Pat. No. 5,026,569. The practical limit of dry grinding is restricted in part by the thermal consequences of such processing on cellulose and in part to the economics of equipment wear and material contamination of the product. Micromilled cellulose (MMC) prepared in aqueous or other liquid media as described in U.S. Pat. No. 4,761,203 avoids the thermal decomposition associated with prolonged or intense dry grinding. This technique allows particle size reduction into the colloidal range (about 10 microns). It is believed to operate by indiscriminate micro-fragmentation of quaternary structure, without incurring the fusion/thermal degrading effects characteristic of dry grinding.

Microfibrillated cellulose (MFC), as disclosed by Turbak et al (U.S. Pat. No. 4,374,702), is principally a mechanical manipulation of refined cellulose from wood pulp at the tertiary level of structure. The process employs high pressure, impact discharge onto a solid surface of a cellulosic dispersion in a liquid medium. This results in a combination of direct energy transfer through high, adiabatic shear gradients generated within the impact domain and secondary effects of such shear (or translational momentum exchange) from solvent cavitation to disassemble suspended cellulose particles. Depending on the extent of processing and preconditioning of the raw material the structural manipulation produces fibril ensembles of disassembled quaternary structure. These highly dispersed fibril structures impart unusual properties to the continuous liquid phase in which they are prepared.

Microcrystalline cellulose (MCC), as disclosed in U.S. Pat. No. 3,023,104, exemplifies structural manipulation which can occur at the secondary level of structure. The process involves selective acid hydrolysis of solvent accessible and amorphous regions of secondary structure in refined cellulose to produce relatively crystalline microdomains that are resistant to further hydrolysis. The dimension of the crystallite domains is on the order of ten to thirty microns. If the never dried crystallite is sheared, it disperses into parallel clusters of microfibrils, reflecting periodic cleavage along a fibril assembly. The microfibril crystallites exhibit high surface area and readily reassociate on drying into a hard, non-dispersible mass.

Furthermore, the production of rayon and cellulose ethers such as cellulose gum (carboxymethyl cellulose, CMC) involves manipulation at the primary level of structure. In the case of rayon the modification is transient and reversible whereby the reconstituted beta-glucan chain spontaneously reassembles into semi-crystalline material that can be spun into fibrils. Cellulose ethers represent a deliberate, irreversible modification whereby the individually formed beta-glucan chains are prevented from reassembly due to the chemical derivatization. A limited variation of such derivatization is that of powdered cellulose wherein the degree of substitution is relatively low, to form e.g. forming carboxymethyl or diethyl aminoethyl cellulose, CM cellulose and DEAE cellulose, respectively. The latter materials are useful as ion exchange media.

SUMMARY OF THE INVENTION

It is an object of this invention to provide a relatively simple and inexpensive means for refining fibrous cellulosic material into a dispersed tertiary level of structure and thereby achieve the desirable properties attendant with such structural change. The cellulosic fiber produced in this way is referred to herein as "microdenominated cellulose (MDC)".

The foregoing object is achieved by repeatedly passing a liquid suspension of fibrous cellulose through a zone of high shear, which is defined by two opposed surfaces, with one of the surfaces rotating relative to the other, under conditions and for a length of time sufficient to render the suspension substantially stable and to impart to the suspension a Canadian Standard Freeness that shows consistent increase with repeated passage of the cellulose suspension through the zone of high shear.

It has now been discovered that microdenominated cellulose can be produced using standard refining equipment, e.g. a double disk refiner, operated in a way differing from the conventional use of this equipment in refining pulp for paper manufacture. Whereas paper manufacture calls for minimum damage to the fiber during refining and a Canadian Standard Freeness consistent with good drainage of water from the pulp, it will be apparent from the following disclosure that use of the same equipment may be employed to achieve the opposite effect, i.e., a high degree of disintegration of the fiber structure, which results in a cellulose product having very high surface area and high water absorbency. The degree of disintegration is sufficiently severe that, as refining continues beyond that level normally used for paper manufacture (a Canadian Standard Freeness value approximating 100), a reversal of the Canadian Standard Freeness values occurs. The reason for this reversal is that the dispersed fiber becomes sufficiently microdenominated that gradually greater amounts of fiber begin to pass through the perforated plate of the Canadian Standard Freeness tester with water, thus leading to a progressive increase in the measured value as refining continues. Continuation of refining ultimately results in essentially all of the refined fiber readily passing through the perforated plate with water. At this stage of processing, the measured Canadian Standard Freeness value is typical of that for unimpeded passage of water through the perforated plate of the test unit.

Whereas a single stage, and at most two stages are used for conventional refiner processing in paper manufacture, the process of this invention requires multiple passages of the pulp through the zone of high shear, which may typically involve ten to forty passages.

In paper manufacture beating or refining increases the area of contact between dispersed fibers by increasing the surface area through dispersion and fibrillation. MDC manufacture applies and extends such processing to a much greater degree. It is believed that the extent of refinement needed to achieve this high degree of fibrillation leads to a concomitant disassembly of tertiary structure, and perhaps even secondary structure. The result is an ultrastructurally dispersed form of cellulose with very high surface area.

The process for preparing MDC is more closely associated with disassembly than it is with the indiscriminate fragmentation used in mechanical comminution or grinding of dried, refined cellulose or micromilling of cellulose in liquid media. It is also quite different from the approaches noted above based on chemical hydrolysis or chemical modification. The product, MDC, is most nearly like microfibrillated cellulose, MFC, produced by high pressure impact discharge of a cellulosic dispersion in a liquid medium onto a solid surface, as disclosed by Turbek et al. However, contrary to the teachings in the Turbek et al patent, to the effect that beating and refining as practiced in the paper industry are relatively inefficient processes since large amounts of energy are expended to gain relatively minor amounts of fiber opening and fibrillation, the opposite appears to be true based on the research leading up to this invention, as will be explained below.

The MDC product of the invention has very high surface area, consisting essentially of thread-like structures (most of which are not discernable with the light microscope). These represent longitudinally oriented clusters of microfibrils with attendant, protuberant ultrastructure emanating from their surfaces. These structures form entangling and interacting networks which lead to a unique form of microscopic compartmentalization for mixtures of discontinuous materials in water or other continuous phase systems. Such behavior results in the formation of interesting viscoelastic characteristics such as gel structure, mouthfeel, textural quality and other properties highly desired in foods, pharmaceutical and cosmetics products.

The product of the invention, MDC, is characterized by a settled volume greater than about 50% after twenty-four hours, as based on 1% by weight aqueous suspension, and water retention greater than about 350%. Procedures for determining the settled volume and water retention values for MDC are described in detail below.

BRIEF DESCRIPTION OF THE DRAWINGS

FIG. 11 is a photomicrograph of the aforesaid oat fiber before refining shown at a magnification of 250 times.

FIG. 12 is a photomicrograph of the aforesaid oat fiber after refining shown at a magnification of 250 times.

DETAILED DESCRIPTION OF THE INVENTION

Figures 1, 2:
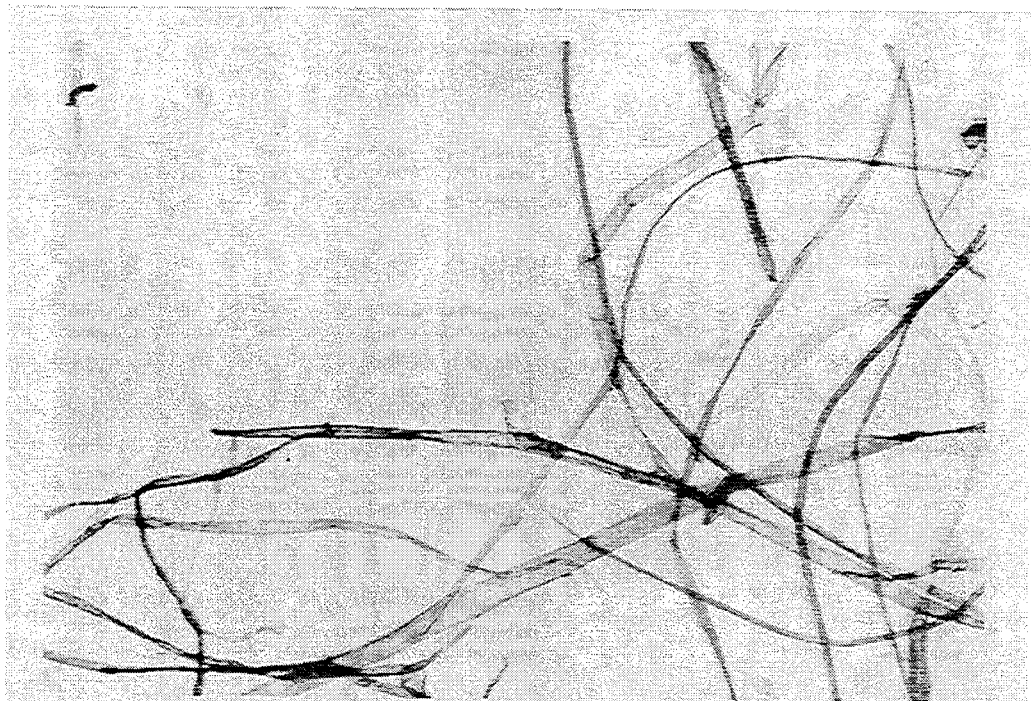
FIG. 1 is a photomicrograph of wheat fiber described in EXAMPLE 1 below before refining shown at a magnification of 100 times.
FIG. 2 is a photomicrograph of the aforesaid wheat fiber after refining shown at a magnification of 100 times.

In accordance with the present invention, microdenominated cellulose is produced from cellulosic material by repeatedly passing the material in an aqueous suspension through a zone of high shear, defined by two opposed surfaces, one of which is caused to rotate relative to the other. According to a preferred embodiment, the cellulose suspension is passed through a double disk refiner of the type typically used in the processing of wood pulps for paper manufacture. Whereas processing with such equipment in conventional paper applications is limited so that the degree of refining achieved corresponds to Canadian Standard Freeness (CSF) values of about 100 or greater, the present invention calls for a degree of refinement whereby the CSF value is reduced toward zero and then progresses through freeness values, approaching and ultimately exceeding the values for never-processed pulp in aqueous suspension.

Examples of the use of this invention are set forth below for softwood pulp, white wheat fiber and oat fiber. Other types of cellulosic fibrous material can also be processed in accordance with the present invention. However, long-fibered materials such as the softwood pulp and wheat fiber appear to be better suited to this approach than short-fibered material.

The starting material for the process is conveniently prepared by beating cellulosic sheet material in a hydrobeater in the presence of a suitable liquid, which disintegrates the sheet material and uniformly disperses the fibers in the liquid.

The exact amount of refining time required to produce MDC depends on the characteristics of the starting material e.g. the fiber length, the temperature of refining and the solids concentration in the pulp. The length of processing is also influenced by the parameters of the shear zone in which the cellulose suspension is processed. In the case of a double disk refiner, these parameters include the amount of back pressure exerted on the cellulose suspension as it is subjected to shear stress during refining, the refiner plate surface configuration, the space between confronting refiner plates, refiner plate diameter and plate peripheral speed. Efficiency is enhanced by operation at high pulp solids concentration, an elevated back pressure on the pulp during refining, elevated pulp temperatures coupled with maximum temperature control, adjustment of the gap between confronting refiner plates by keying on a pre-selected value of amperage to the refiner motor and a refiner plate configuration and peripheral speed that promotes "rubbing" or fraying rather than cutting. Although refining proceeds most efficiently as the solids concentration in the pulp is increased, however, there is a limit to how high the solids concentration can be and still have the pulp flow through the system. A short-fibered material like oat can be concentrated to almost twice the solids concentration possible with softwood and wheat, both long-fibered materials.

Preferred operating conditions for preparation of MDC in a double disk refiner are as follows: fiber length of about 50 to 3000 microns, or greater; refining temperature of about 60° F. to about 200° F.; a solids concentration of about 2 to about 10% by weight of the cellulose suspension; and back pressure of about 10 to about 40 psi.

The remaining parameters, including plate configurations, spacing between adjacent plates, plate diameter and peripheral plate speed will depend on the particular model of refiner selected to process the MDC. A typical run employing a Black Clawson 28-inch Twin Hydradisc refiner is exemplified below.

A primary indicator used to monitor the extent of refining of the cellulosic material is the Canadian Standard Freeness value as measured using test equipment and procedures contained in TAPPI 227 "Freeness of Pulp" J. Casey, *Pulp and Paper* (1980). Freeness has been shown to be related to the surface conditions and the swelling of fiber which influences drainage. As refining continues beyond levels normally practiced in conventional paper making, the dimensions of the resulting structures become sufficiently small such that a reversal of freeness values occurs, i.e. increasing rather than diminishing values of freeness as refining continues. This anomalous rise of freeness is referred to herein as "false freeness". Once the reversal occurs and refining continues thereafter, the measured freeness value increases until a maximum value of approximately 800 is reached. At this point the refined material has been rendered sufficiently supple and fine (dimensionally small) that it readily passes through the perforations of the perforated plate of the tester along with the water. In other words, the suspension behaves as though it were fiber-free water of the same total volume as the fiber-containing sample being measured. This is the limiting condition for obtaining meaningful data from freeness measurements. As the cellulose suspension achieves this desired level of freeness, it becomes substantially stable, which is intended to mean that there is no visible segregation of the continuous phase from the disperse phase, even upon standing for a reasonable period of time.

Figure 3:
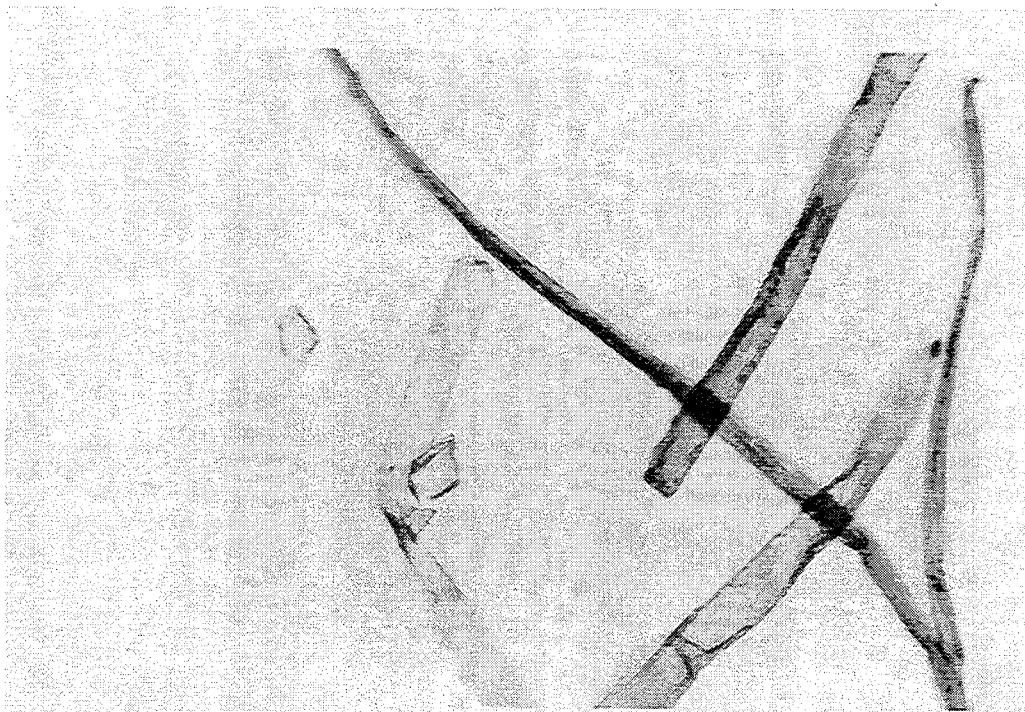
FIG. 3 is a photomicrograph of the aforesaid wheat fiber before refining shown at a magnification of 250 times.
Figure 4:
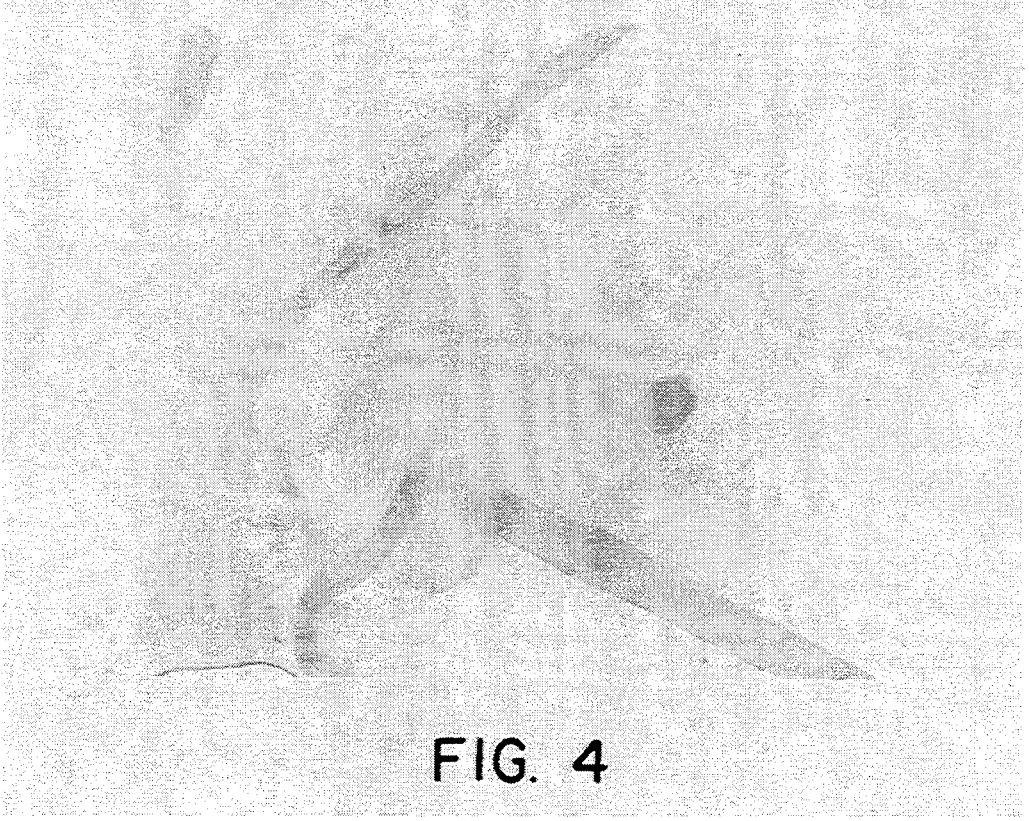
FIG. 4 is a photomicrograph of the aforesaid wheat fiber after refining shown at a magnification of 250 times.

Examination of photomicrographs of fiber samples provide insight as to the degree of fibrillation that is achieved by refining, with reference to the starting material. FIG. 1 shows that the length of the fiber prior to refining is in most cases at least 1000 microns and the fiber width is one to two microns. Shown in FIG. 2 is the wheat fiber structure resulting from the refining process described in EXAMPLE 1, below, at a magnification of 100 times. FIG. 3 and FIG. 4 show the wheat fiber at a magnification of 250 times and reveal detail regarding the refined fiber in FIG. 4. It is apparent from FIG. 2 and FIG. 4 that the refined fiber is highly disassembled. There is no evidence of the original quaternary structure shown in the fiber before refining. It has been disintegrated by the extended period of refining and replaced by a network of fibrils of vastly increased surface area. These fibrils as viewed in the light microscope, appear as very long threadlike strands of extremely small diameter for those that can be seen.

Figure 5:
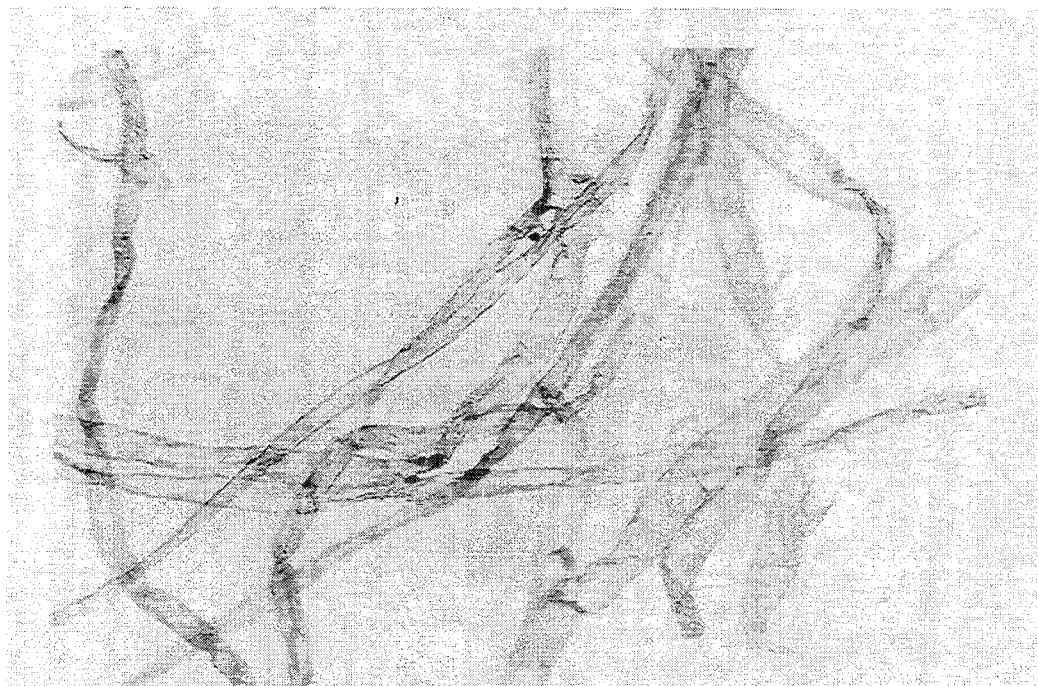
FIG. 5 is a photomicrograph of softwood fiber described in EXAMPLE 2 below before refining shown at a magnification of 100 times.
Figure 6:
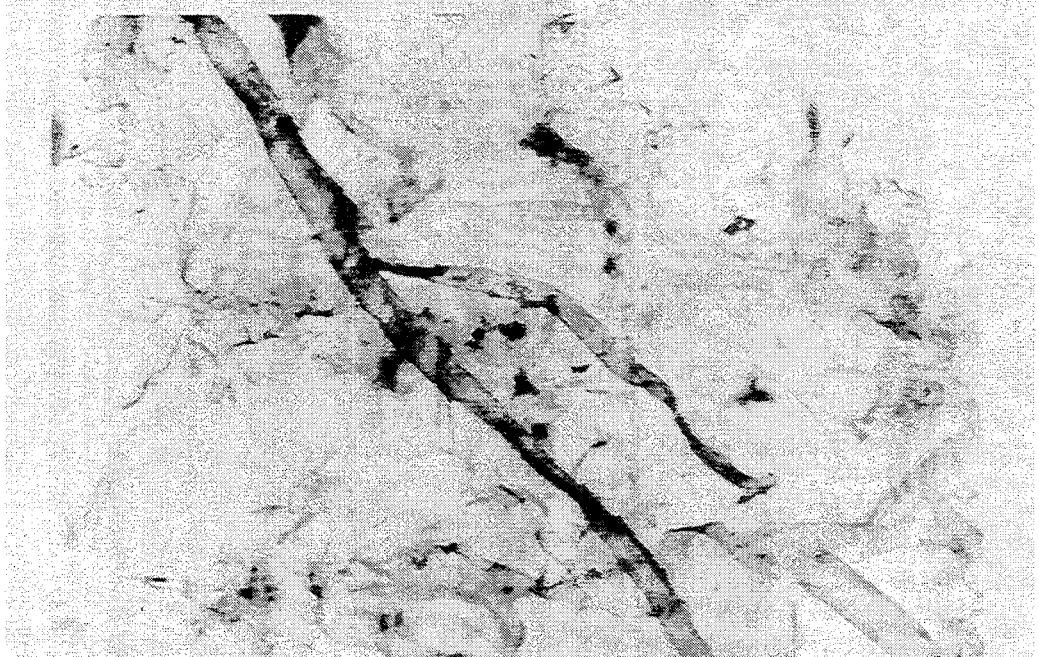
FIG. 6 is a photomicrograph of the aforesaid softwood fiber after refining shown at a magnification of 100 times.
Figure 7:
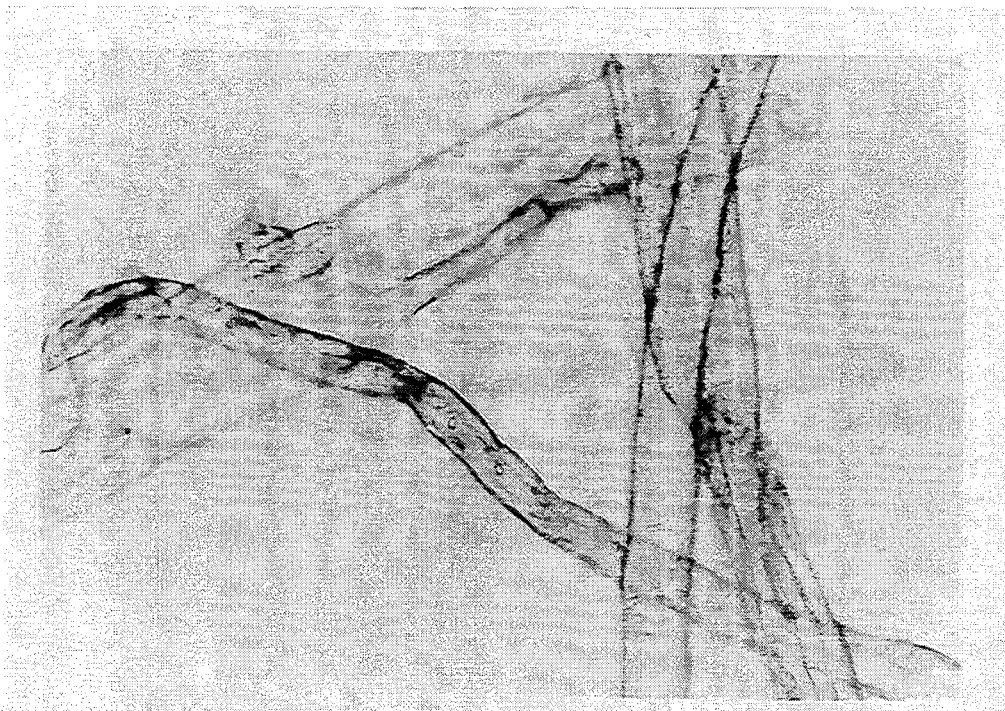
FIG. 7 is a photomicrograph of the aforesaid softwood fiber before refining shown at a magnification of 250 times.
Figure 8:
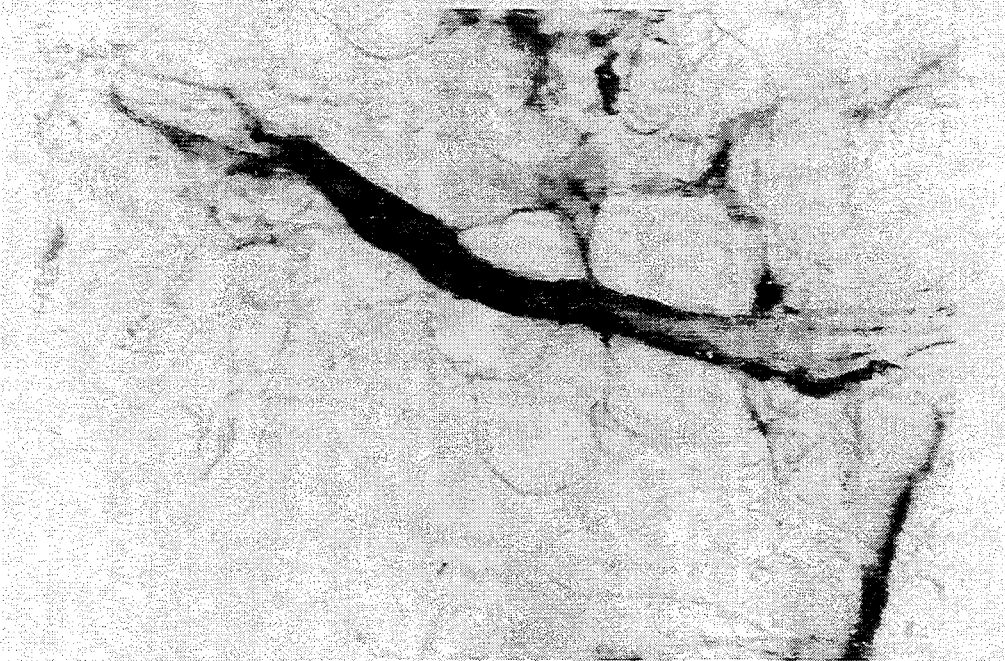
FIG. 8 is a photomicrograph of the aforesaid softwood fiber after refining shown at a magnification of 250 times.

FIG. 5 shows the fiber structure of softwood fiber at a magnification of 100 times before refining and reveals a somewhat longer length (1000 to 3000 microns long) and greater width (two to four microns wide) than the wheat fiber described above. FIG. 6 and FIG. 8 show fiber structure for the refined softwood that appears to be quite similar to that of the wheat fiber sample discussed above.

Figure 9:
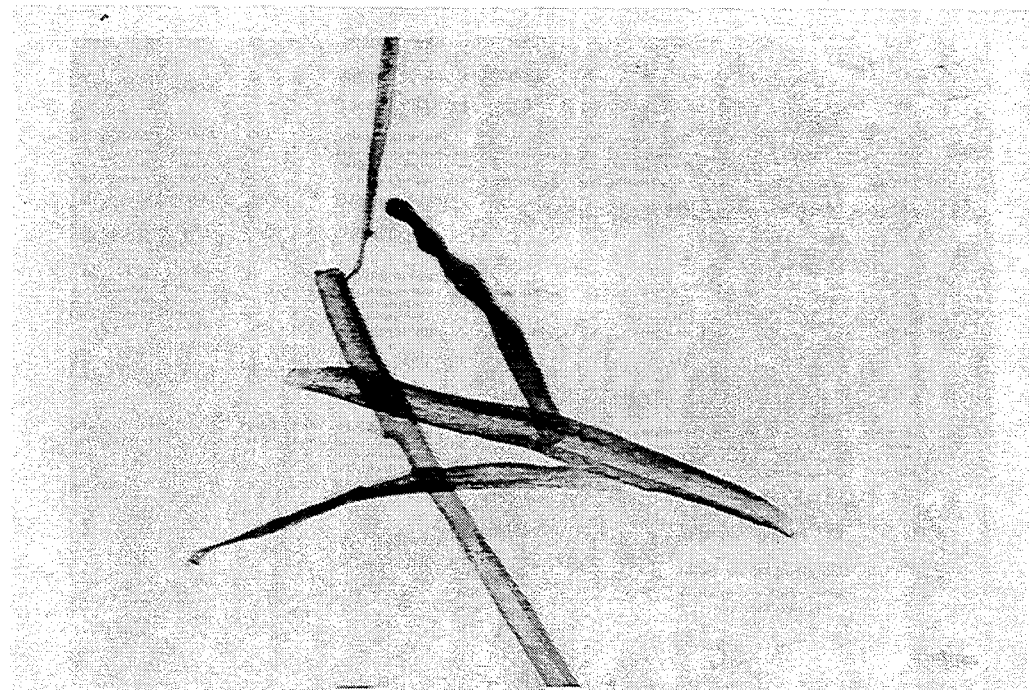
FIG. 9 is a photomicrograph of oat fiber described in EXAMPLE 3 below before refining shown at a magnification of 100 times.
Figure 10:
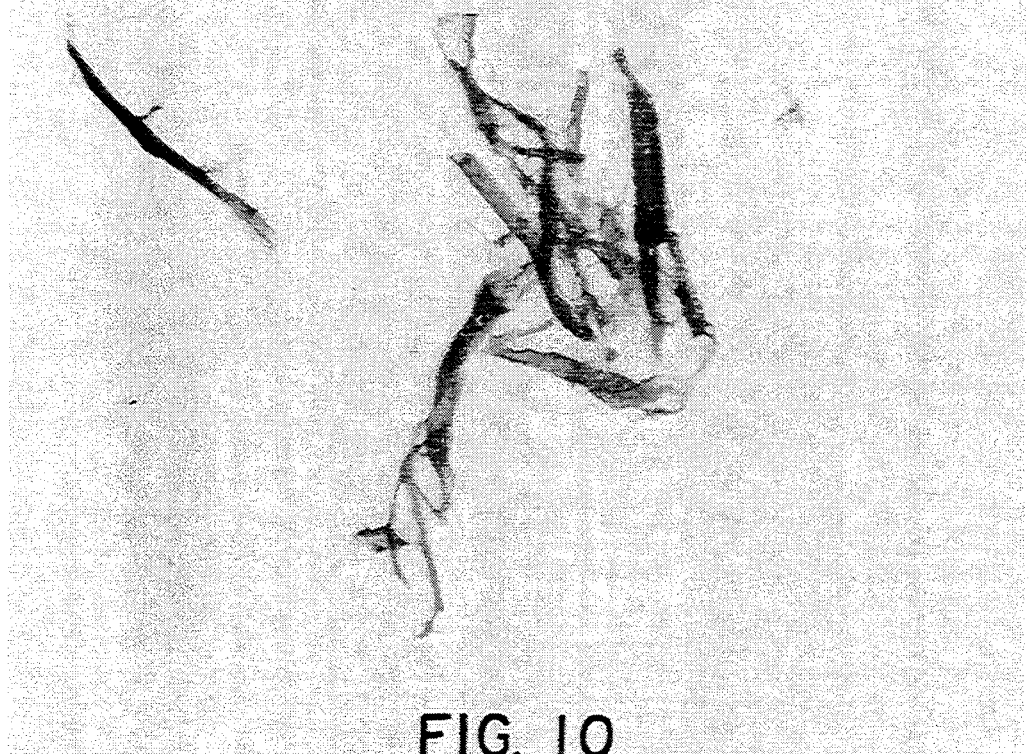
FIG. 10 is a photomicrograph of the aforesaid oat fiber after refining shown at a magnification of 100 times.
Figures 11, 12:
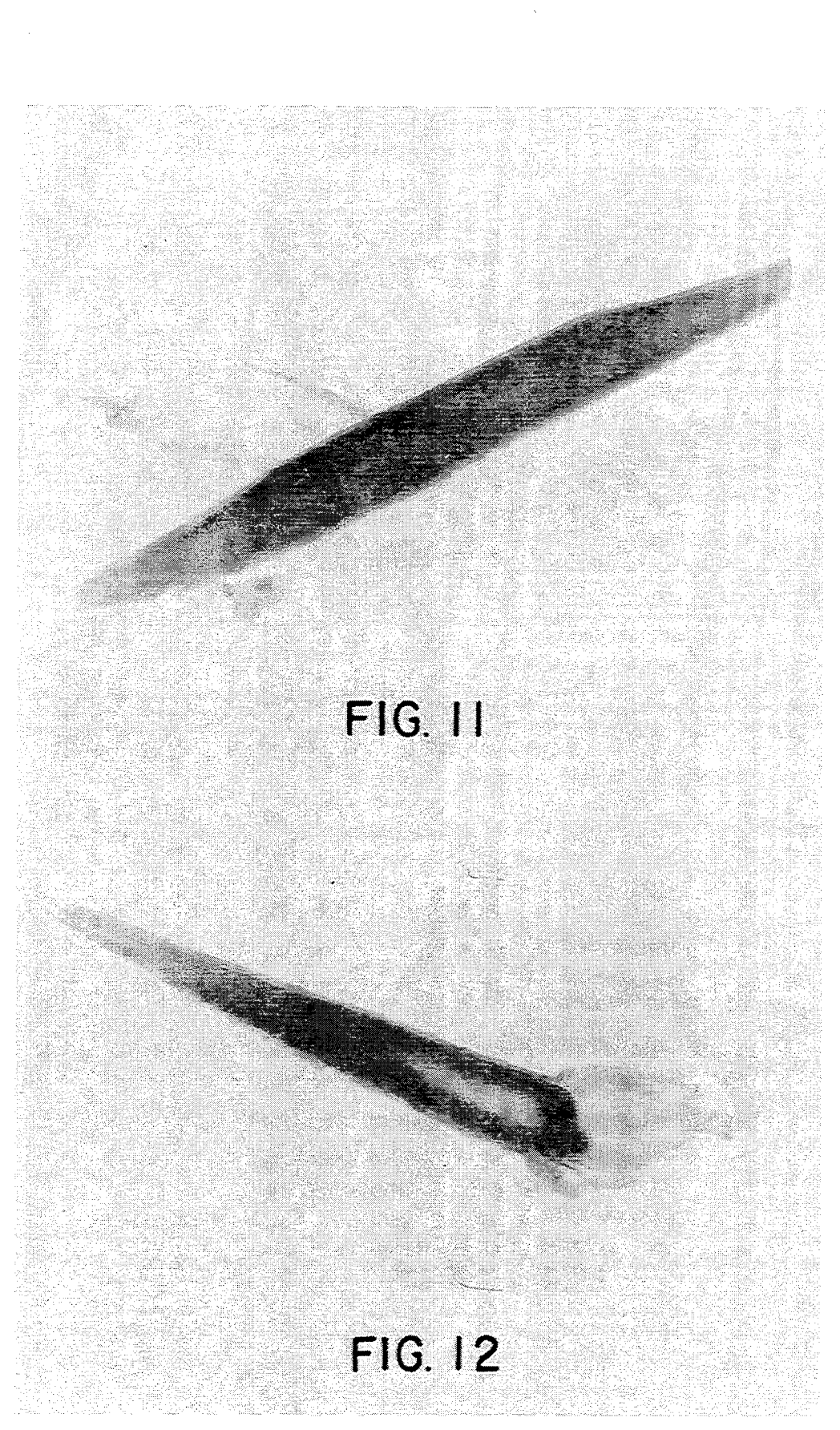

Examination of photomicrographs of oat fiber samples provide insight as to the influence of fiber length of the starting material on the degree of fibrillation achieved by refining as compared to the longer fiber starting materials. FIG. 9 shows the oat fiber prior to refining to be between 500 and 1000 microns in length and two to four microns in width. FIG. 10 and FIG. 12 show that refined oat fiber structure undergoes disassembly but not to the degree of the long fibered wheat and softwood samples. There is some evidence of the original quaternary structure shown in the fiber before refining. A smaller percentage of the structure of oat fiber has been converted to a network of fibrils. This has resulted in less surface area being created than occurs when long fibered materials are refined.

As will be appreciated from the foregoing description, MDC is the result of disassembly of cellulose structure via essentially physical manipulation. As such, MDC is distinguishable from cellulosic products produced by chemical transformation. No appreciable chemical change of the cellulose starting material occurs during the refining process described herein.

Several other parameters or properties, in addition to Canadian Standard Freeness, serve to characterize MDC.

A parameter useful in the characterization and description of MDC is the settled volume of aqueous dispersions of differing solids content after twenty-four hours of settling. The settled volume of a sample of MDC is determined by dispersing a known weight of cellulose (dry weight basis) in a known amount of water, e.g. in a graduated cylinder. After a prescribed settling time, the volume of the bed of suspended cellulose is measured with reference to the total volume of the continuous aqueous phase. The settled volume is expressed as a percentage of the bed volume to the total volume. From this data the solids concentration in an aqueous dispersion that results in a settled volume that is fifty percent of the original volume can be determined and used to characterize the product. The results of such measurements are shown in Table 1. Ultrastructural parameters are also important in this characterization. The very long fibril softwood has the lowest solids concentration for 50% settled volume at 0.18%. The intermediate wheat fiber is next at 0.23% and oat fiber with a very short fibril is highest at 0.87%. A characteristic of MDC is that a 1% by weight aqueous suspension has a settled volume greater than 50% after twenty-four hours.

TABLE 1

| Example Number | Fibrous Material | False Value of CSF (ml) | Viscosity at 1.5 Wt. % (cp) | 50% Settled % Water Volume Wt. | % Retention |
|---|---|---|---|---|---|
| 1 | Wheat | 780 | 5,860 | 0.23 | 1,005 |
| 2 | Softwood | 730 | 7,850 | 0.18 | 1,110 |
| 3 | Oat | 810 | 1,300 | 0.76 | 569 |

Water retention is another parameter for characterizing MDC. Water retention values are determined by employing a pressure filtration apparatus (Baroid Model 301 for low pressure fluid loss control measurements, N. L. Baroid Corporation, Houston, Tex.) routinely used to evaluate drilling fluid properties. A 100 gram aliquot of a nominal 4 to 8% w/w aqueous dispersion of cellulose is loaded into the filter cell chamber, the cell chamber is capped and subjected to 30 psig. pressure from a regulated nitrogen source. The water discharged from the filtration cell chamber is collected and pressure continued for thirty seconds after observation of the first gas discharge. The nitrogen source is then turned off and collection of discharged water continued for one minute or until the gas discharge ceases, whichever event occurs first. Basically the technique employs pneumatic, pressure filtration to remove interstitial water from the particulate phase.

The expressed volume of water is recorded along with the weight of wet cake. The wet cake is then dried for sixteen hours at 95 degrees Centigrade or until a constant weight is recorded. The water retention value is computed as the ratio of (wet cake weight minus the dry cake weight) to (dry cake weight) times 100. This technique provides a good estimate of the capillary and absorptive retention of water by the cellulose solids by removing the interstitial water from the cake solids. The procedure is quick (5 to 10 minutes) and highly reproducible. The water retention value of MDC is characteristically at least 350%, and preferably at least 500%.

Viscosity may also be used as a characterizing property of MDC. Apparent viscosities of an aqueous dispersions of 1.5% w/w MDC solids samples were determined with a Brookfield Viscometer model DV-III using spindle SC4-16 with the small cell adapter at a number of shear conditions (5 through 100 RPM). The samples were pre-dispersed by high speed mixing for three minutes at 10,000 RPM with a rotor stator type mixer (Omni International, model 1000). The viscosities measured for final refined product (MDC) of the three examples are shown in Table 1. The softwood fiber product exhibited a viscosity of approximately 8,000 centipoise at a spindle speed of 100 RPM. The white wheat fiber product had a viscosity of approximately 6,000 and the oat fiber a viscosity of approximately 1,300 at the same measurement conditions as for the softwood fiber. It appears the wide range in the measured viscosities is primarily due to the differences in fibril length and other ultrastructural characteristics of the starting materials.

It should be understood that the above viscosity measurements on MDC dispersions are made on a heterogeneous mixture (an interacting particle ensemble suspended in a fluid medium). Viscosity measurement is normally applied to homogenous systems. Because of the heterogeneous nature of the mixture a certain degree of mechanical distortion occurs in the mixture around the rotating spindle used to determine shear stress forces within the mixture. Consequently shear/shear stress measurements are time and history dependent. As such the measurement is not a true viscosity in the conventional sense but rather provides a reproducible measurement that has been found useful for characterizing the degree of microdenomination and in describing the implementation of this invention.

Energy input for refining MDC in the manner described herein ranges from about 0.5 to about 2.5 kilowatt-hours per pound of MDC (dry weight basis) and associated refining times vary from two to eight hours depending on the cellulosic material being processed. This is significantly lower than the energy requirements for microfibrillated cellulose as reported by Turbak et al in U.S. Pat. No. 4,483,743. Based on five to ten passes of a 1% MFC solids aqueous dispersion through an 80% efficient homogenizer at 8,000 psig. the energy requirement ranges from 4.4 to 8.7 kilowatt-hours per pound of MFC.

The following examples are provided to describe in further detail the preparation of MDC in accordance with the present invention. These examples are intended to illustrate and not to limit the invention.

EXAMPLE 1

Never dried white wheat fiber was mixed with 2,190 gallons of water in a hydrobeater (Black Clawson Model 4-SD-4 with Driver No. 45) to make up a pulp of 4.5% w/w solids. The white wheat fiber used in this example is a commercially available refined fiber product derived from bleached wheat chaff obtained from Watson Foods Company, West Haven, Conn. The white wheat product was obtained as a nominal 40% w/w nonvolatile solids fiber mat. The product was stated to be 98% total dietary fiber by the Prosky method. The particle size by microscopic examination indicated a largely heterogeneous population of thin needle-like sclerchyma cells ranging in major/minor dimensions of 500 to 1000 / 10 to 20 microns with few interspersed parenchyma cells of 200/50 microns.

After beating the pulp for twenty minutes at room temperature it was transferred to a water jacketed holding tank to be repeatedly passed through a Black Clawson Twin Hydradisc refiner. The refiner of this example is a twenty-eight inch diameter double disc unit powered by a 250 horsepower motor. The refiner plates mounted on the discs are made of sharloy (a nickel hardened steel). The refiner plates were not equipped with dams. The faces of the particular refiner plates used in this refiner consists of alternate bars and grooves oriented so that bars of the adjacent refiner plates (one static and the other revolving) move relative to one another with a scissoring action occurring as the bars of each confronting plate move past one another. The three critical dimensions of these bars and grooves are the bar width, channel width and channel depth. For this particular unit, they were, respectively, 2/16 of an inch, 4/16 of an inch and 3/16 of an inch (expressed as 2,4,3 by Black Clawson's convention).

The refiner plates on the revolving disc move at 713 revolutions per minute. Based on the outer periphery of the refiner disc extending to 13 and ¼ inch from the centerline of the drive shaft, this corresponds to peripheral speed of about 4,900 feet per minute. The pulp was continuously circulated at a rate of approximately 250 gallons per minute through the refiner and back to the holding tank. Passage of the cellulose suspension through the refiner occurs so as to have equal flow on each side of the revolving disc.

One disc of the refiner is fixed while the other is sliding. This allows the distance between adjacent discs to be adjusted. In the full open position (typical of startup or shutdown), discs are one and three-quarters inch apart. During refining, the discs are of the order of one to two thousands of an inch apart. Rather than adjust the gap between discs to a specific spacing, the value of the amperage to the motor driving the refiner is used to establish spacing. The procedure upon startup is to move the discs from the full open position to a closer position where the amperage reading increases until it reaches 310 amps. At this point, maximum power is being delivered from the motor. Once this point is reached, the back pressure on the refiner is increased by closing down the valve on the line returning pulp from the refiner to the holding tank. The back pressure is normally raised from an initial value of about 14 psig to a final value of about 35 psig. As the back pressure is increased without adjustment of the sliding disc location, the amperage drawn by the motor decreases to about 260 amps. With the back pressure at 35 psig, the sliding disc is adjusted to bring the discs closer together until the desired 310 amps are drawn by the motor. Once this is done, there is no further adjustment of the sliding disc unless the motor amperage drops significantly. This may occur as refining proceeds if certain properties of the pulp change significantly. In that event, the sliding disc is moved to reduce the gap between the discs until either the desired amperage is once again achieved, or the discs begin to squeal. Squealing is to be avoided as it is indicative of excessive disc wear and leads to high refiner plate replacement costs.

A gate-type mixer in the holding tank continuously mixed the contents during refining. A back pressure of 34 pounds per square inch was maintained in the return line from the refiner outlet to the holding tank. The recycle operation continued for approximately six hours during which the Canadian Standard Freeness of the pulp changed from an initial value of 190 to a final "false" value of 780 ml.

During refining the temperature of the pulp increased from an initial value of 64 to a final value of 190 degrees Fahrenheit. The amperage drawn by the 250 horsepower motor of the refiner varied from 310 initially to 290 amperes at completion of refining. Energy input to the refiner was approximately 1.2 kilowatt-hours per pound of refined fiber processed (dry weight basis). The resulting product is characterized in TABLE 1.

EXAMPLE 2

Dry, softwood fiber used in this example was obtained from Stora Forest Industries Ltd., Port Hawkesbury, Nova Scotia, Canada as a bleached sulfite pulp. It was derived from softwood species (balsam fir and black and white spruce). The bleaching sequence was reported to be (D70+D70) E (DE) D. The ash (TAPPI 211 and 85) is 0.6% and the CSF 660. The dispersed individual fibers appeared to be 20 to 25 microns in diameter and ranged from one to three mm. in length with the average fiber 25 microns by 2 mm.

Sheets of dry, softwood fiber (Storafite 04-620972) were mixed with 2,080 gallons of water in the same hydrobeater as used in EXAMPLE 1 to make up a pulp of 3.7% solids. After beating the pulp for twenty minutes at room temperature it was transferred to the holding tank to be repeatedly passed through the same Black Clawson refiner as used in EXAMPLE 1. Pulp was circulated at a rate of approximately 250 gallons per minute through the refiner and back to the holding tank. A gate-type mixer continuously mixed the contents of the holding tank during refining. A back pressure of 34 pounds per square inch was maintained in the return line from the refiner outlet to the holding tank. The recycle operation continued for approximately six hours during which the Canadian Standard Freeness of the pulp changed from an initial value of 620 to a final "false" value of 730 ml.

During refining the temperature of the pulp increased from an initial value of 64 to a final value of 144 degrees Fahrenheit. The amperage drawn by the 250 horsepower motor of the refiner varied from 310 initially to 290 amperes at completion of refining. Energy input to the refiner was approximately 2.4 kilowatt-hours per pound of refined fiber processed (dry weight basis).

EXAMPLE 3

Dry oat fiber (Williamson Type 9780) was mixed with 1,055 gallons of water directly into the holding tank for the refiner to make up a pulp of 7.86% solids. The dry oat fiber used in this example is a commercially available refined fiber product derived from bleached oat hulls (from Opta Food Ingredients, Inc. in Cambridge Mass.). The product, identified as Better Basics TM type 780, is stated to be 98% total dietary fiber by the Prosky method. It was obtained as a dry, light tan colored powder that was readily hydrated in the refiner tank prior to refining. The particle size was such that 98% on a weight basis passed through a 50 mesh screen using an Alpine Airjet Sieve. Microscopic examination indicated particles consisted largely of heterogeneous dispersed fiber cells with major/minor dimensions of 100 to 600 / 10 to 40 microns. In contrast to wheat and softwood oat represents a relatively short fiber structure.

The already finely divided state of the oat fiber made it possible to eliminate the hydrobeater step. The pulp was refined in the same Black Clawson unit as used in the two previous examples. Pulp was circulated at a rate of approximately 250 gallons per minute through the refiner and back to the holding tank. A gate-type mixer in the holding tank continuously mixed the contents during refining. Back pressure maintained in the return line from the refiner outlet to the holding tank varied from 34 to 31 pounds per square inch gauge. The recycle operation continued for two hours and forty minutes during which the Canadian Standard Freeness of the pulp changed from an initial value of 310 to a final "false" value of 810 ml.

During refining the temperature of the pulp increased from an initial value of 65 to a final value of 168 degrees Fahrenheit. The amperage drawn by the 250 horsepower motor of the refiner varied from 310 initially to 260 amperes at completion of refining. Energy input to the refiner was approximately 0.5 kilowatt-hours per pound of refined fiber processed (dry weight basis).

While certain preferred embodiments of the present invention have been described and examplified above, it is not intended to limit the invention to such embodiments, but various modifications may be made thereto, without departing from the scope and spirit of the present invention as set forth in the following claims.

We claim

1. A process for preparing microdenominated cellulose comprising repeatedly passing a liquid suspension of fibrous cellulose through a zone of high shear, said zone being defined by two confronting refining disk surfaces, with one of said surfaces rotating relative to the other, under conditions and for a length of time sufficient to render said suspension substantially stable and to impart to said suspension a Canadian Standard Freeness that shows consistent increase with repeated passage of said cellulose through said zone of high shear.

2. A process as claimed in claim 1 wherein said suspension is passed through a zone of high shear defined by confronting disk surfaces of a double disk refiner.

3. A process as claimed in claim 1 wherein said suspension contains 2 to 10% by weight of cellulose.

4. A process as claimed in claim 1 wherein said suspension is an aqueous suspension.

5. A process as claimed in claim 1 wherein said liquid suspension is maintained at an elevated temperature no greater than 200° F.

6. A process as claimed in claim 1 wherein a back pressure of at least 30 psig is exerted on said liquid suspension in said zone of high shear.

7. A process as claimed in claim 1 wherein said liquid suspension of fibrous cellulose material is prepared by beating sheets of cellulose in a hydrobeater in the presence of said liquid.

* * * * *